United States Patent [19]

Gomes et al.

[11] Patent Number: 4,570,637
[45] Date of Patent: Feb. 18, 1986

[54] ELECTRODE

[75] Inventors: Robert L. Gomes, West Boxford; Joseph P. Maffione, Cambridge, both of Mass.

[73] Assignee: Andover Medical Incorporated, Lowell, Mass.

[21] Appl. No.: 543,695

[22] Filed: Oct. 20, 1983

[51] Int. Cl.$^4$ .......................... A61B 5/04; A61N 1/04
[52] U.S. Cl. .................................. 128/639; 128/641; 128/803
[58] Field of Search ............... 128/783, 798, 802, 803, 128/639–641, 643, 644

[56] References Cited

U.S. PATENT DOCUMENTS 3,977,392 8/1976 Manley ................................ 128/641
4,166,453 9/1979 McClelland ....................... 128/639
4,243,051 1/1981 Wittemann ..................... 128/802 X
4,422,461 12/1983 Glumac ................................ 128/798

Primary Examiner—Lee S. Cohen
Attorney, Agent, or Firm—Grady J. Frenchick; Joseph F. Breimayer; John L. Rooney

[57] ABSTRACT

An improved medical electrode is particularly adapted for transmitting DC currents. The electrode includes (1) an electrically conductive substrate electrically connected to a stud member and chemically inert with respect to the electrically and ionically conductive material, such as a gel, coupling the electrode to the skin of the user, and (2) a predetermined amount of an electrically-conductive material, preferably silver, disposed on the substrate in spaced relationship to the stud member and interfacing with the electrically and ionically conductive material.

12 Claims, 12 Drawing Figures

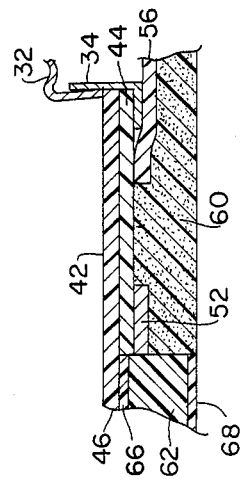
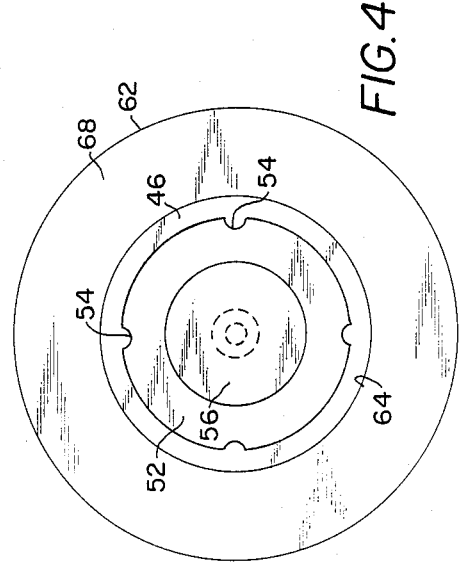
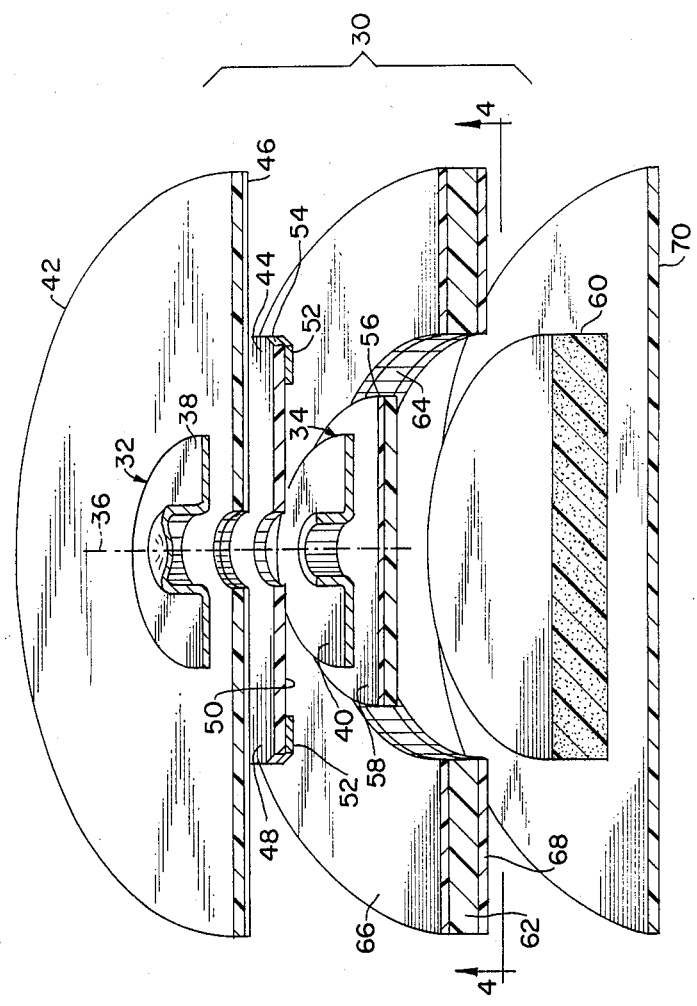

ELECTRODE

BACKGROUND OF THE INVENTION

The present invention relates generally to medical electrodes of the type adapted to be attached to the skin, and more particularly to improved medical skin electrodes for use in both measuring biological or physiological potentials and transmitting stimulating currents.

As is well known, biological or physiological potentials can be sensed at the skin of a living body by using a pair of electrodes spaced apart at select locations on the body (such locations being dependent on the type of potentials being measured), and can be recorded by appropriate instrumentation. For example, these electrodes can be used to monitor and record cardiopotentials from the chest and limbs, electrooculographic signals indicating eye motions by applications to appropriate positions on the face, transthoracic impedance differentials indicating apneic spells, as well as employed for long term testing and monitoring such as Holter cardiac arythmia stress testing.

In recent years, various techniques have been developed in promoting healing within the body by using a stimulating current and which utilize one or more medical electrodes attached to the skin. For example, one such technique can be used with rather a high rate of success in promoting healing of fracture nonunions. One instrumentation system which has been developed to promote osteogenesis, where bone fragments otherwise fail to join together, is commercially-available from Zimmer, USA of Warsaw Ind. under the name "Direct Current Bone Growth Stimulator". The stimulator provides a constant direct current directly at the site of a fracture nonunion through percutaneously placed cathodes. The cathodes are in the form of a plurality of pins whose ends are inserted percutaneously and typically disposed in the nonunion site. The anode of the system is in the form of an electrode pad suitably disposed on the skin in a selected location so that when a constant direct current power supply is properly connected to the cathode pins and anode pad the appropriate approximate current level, typically at about 80 microamps, is generated in the region of the nonunion.

Development of such direct current stimulation devices has created problems associated with available electrodes for use as anode pads. More specifically, presently available standard electrodes typically include a stud member for connection to an electrical lead. The stud member usually extends through a sheet of adhesive to a pad of porous material preloaded with an electrically-conductive gel so that the electrode can be attached to the skin maintaining the gel in contact with the skin while at the same time exposing the stud member so that it can be connected to an electrical lead. The stud member of at least some commercially available electrodes typically is made of an electrically nonconductive material, such as a polymeric plastic, to form a core. The plastic core is then coated with a layer of silver, which provides a good electrically-conductive path between the electrical lead and the gel material with the interface between the silver and gel providing a sufficiently low impedance path.

The gel material typically contains an agar solution of dissolved sodium chloride so that the gel is completely compatible with the skin and generates a minimum of motion artifacts when in operation.

The chemistry of such an electrode stud member and gel is therefore such that an ionization reaction occurs when a current flows through the electrode and gel. Specifically, the dissolved salt provides $Na^+$ and $Cl^-$ ions in the gel solution. When applying an AC signal, the silver oxidizes and reacts with the chloride to form silver chloride (with silver atoms losing electrons to form $Ag^+$ ions and the $Ag^+$ ions and $Cl^-$ ions combining to form silver chloride) when the signal is of one polarity and reduces to form silver and chloride ions when of the opposite polarity (with $Ag^+$ and $Cl^-$ ions being formed from the silver chloride and an electron being added to the $Ag^+$ ion to form silver once again). The net result after each cycle of current is that the electrode remains substantially unchanged. When a DC signal is applied however, a continual reduction or continual oxidation reaction will occur. When using the electrodes to detect biological or physiological signals these reactions are practically insignificant since high impedance instruments are used to detect these signals so as to draw very small currents. As such the reactions are extremely slow. In the situation, however, where large DC currents (such as those currents generated by the Zimmer stimulator) are transmitted through an electrode used as an anode pad, a continual oxidation reaction of the silver would occur so as to form silver chloride. As silver chloride is formed the impedance at the interface between the gel and the silver chloride increases to the point where the electrode no longer is useful since a current drop through the electrode will occur.

Although the silver coated stud members of the previously described electrodes have been made with a precise amount of silver, it has been found that these electrodes function inadequately as anode pads. The surface area of the stud member that interfaces with the gel is relatively small such that the useful life of the electrode becomes somewhat unpredictable Further, while in use, over prolonged periods of use pressure on the stud member against the skin tends to force the gel away from the stud member so as to jeopardize the low impedance current path between the silver of the stud member and the gel, thereby increasing the impedance of that electrical path.

SUMMARY OF THE INVENTION

It therefore is a principal object of the present invention to provide an improved electrode which can be used with large DC currents.

Another object of the present invention is to provide an improved electrode for use with relatively large DC currents and having a predetermined intended useful operating lifetime.

And another object of the present invention is to provide an improved electrode for use with relatively large DC currents having a relatively low impedance over its useful operating lifetime.

Yet another object of the present invention is to provide an improved electrode for detecting biological or physiological signals which electrode is equally as useful as an anode pad.

Still another object of the present invention is to provide an improved anode pad for use with a system for promoting osteogenesis.

And yet another object of the present invention is to provide an improved studded medical electrode constructed such that pressure on the stud against the skin aids in placing the electrically conductive material coupling the electrode to the skin in the electrical pathway.

These and other objects are achieved by an improved medical electrode assembly adapted for use with an electrically conductive material for coupling the electrode assembly to the skin of the user. The assembly, being of the type including a stud member, comprises an electrically conductive substrate electrically coupled to the stud member and chemically inert to the coupling material. A layer of an electrically conductive material, such as silver ionically reactive with the coupling material when current is transmitted therebetween, is disposed on the substrate, physically spaced from the stud member and adapted to electrically interface with the coupling material so as to define an electrical path from the gel through the layer and the substrate to the stud member. Preferably, the layer is disposed in a ring-shaped pattern concentrically about the stud member so that pressure of the stud member against the skin forces the coupling material radially toward the ring-shaped layer. The assembly is particularly useful for DC current levels at about 80 microamps.

Other objects of the present invention will in part be obvious and will in part appear hereinafter. The invention accordingly comprises the product possessing the features, properties and relation of components which are exemplified in the following detailed disclosure, and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawings wherein:

FIG. 3 is an exploded perspective view taken in cross-section of the first embodiment of the electrode of the present invention;

FIG. 4 is a bottom view of the electrode of FIG. 3 taken along section line 4—4 of FIG. 3;

FIG. 5 is a radial cross-sectional view of the electrode assembly of FIG. 3, partially cut-away, and assembled for use;

DESCRIPTION OF THE PREFERRED EMBODIMENT(S)

Figure 1A:
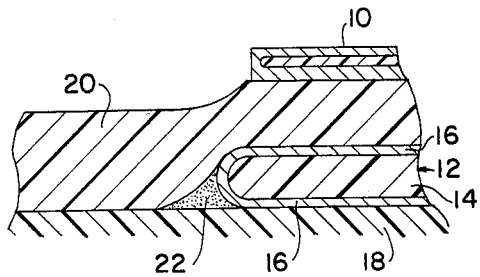
FIGS. 1A-1C illustrate in sequence as a function of time the ionization reaction of a standard type prior art electrode.

In the drawings, the same numerals are used in the various Figs. to designate similar or like parts.

Figure 2:
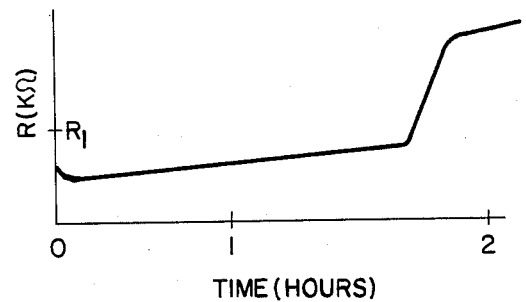
FIG. 2 is a graphical illustration of the effect of the ionization reaction on the impedance of the electrode as illustrated in FIGS. 1A-1C.
Figure 1B:
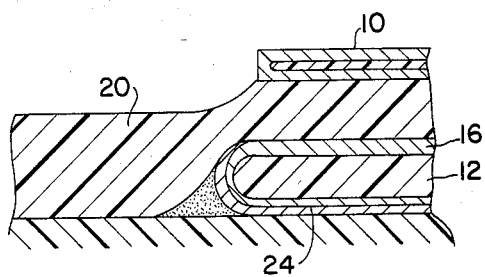
Figure 1C:
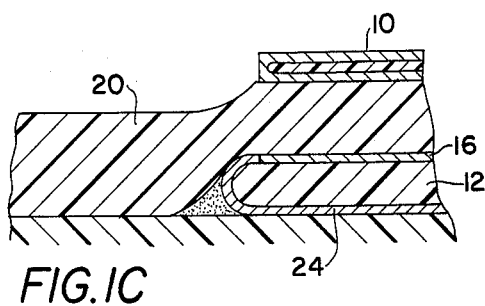

Referring to FIG. 1, the section of a typical standard electrode shown includes a stud member having a stud 10 and an eyelet 12. Stud 10 and eyelet 12 are secured together with an adhesive sheet 20 therebetween. Eyelet 12 includes core portion 14 of, for example, a non-conductive material which is coated with an electrically conductive layer 16, typically silver. Eyelet 12 contacts porous pad 18 containing electrically conductive gel 22 such as an agar solution of sodium chloride. As shown in FIG. 1A, silver 16 has a predetermined thickness when new and interfaces with gel 22 to provide a relatively low electrical resistance to DC current as shown in FIG. 2 at $t=0$. Subjecting the electrode to a relatively high DC current, for example 80 microamps, so that current flows from the stud member through gel 22, creates an ionization reaction so that silver atoms of silver 16 each give up an electron, resulting in an $Ag^+$ ion. The latter in turn combines with a $Cl^-$ ion provided by gel 22. Thus silver in layer 16 begins to be converted to silver chloride as indicated at 24 in FIG. 1B. The resistance increases as shown at $t=1$ in FIG. 2. Continuing the current level, eventually all of the exposed silver of the eyelet will be converted to silver chloride as shown in FIG. 1C resulting in a large increase in resistance as shown at $t=2$ in FIG. 2. Where the usefulness of the electrode is dependent upon its resistance below a certain level such as $R_1$ in FIG. 2, it is apparent that the electrode will be unusable well before the time $t=2$. The increase in resistance well before the complete conversion of the exposed silver to silver ions is due in part to the limited surface area, offerred by the stud member, which interfaces with the gel.

In accordance with the present invention a relatively thin layer of a predetermined amount of an electrically conductive material, preferably silver, is disposed on an electrically conductive substrate. The latter is electrically connected to the stud member of the electrode. The thin layer is disposed in a predetermined manner so as to provide a greater surface ara, which interfaces with the electrically conductive coupling material, such as a gel (disposed between the electrode and the skin of the body to which the electrode is attached), than otherwise provided by the exposed portion of the stud member of the prior art.

More particularly, referring to FIG. 3, the electrode 30 of the embodiment illustrated is shown cut in half along its diameter and includes a stud member comprising the stud 32 and eyelet 34, both being described with respect to an elongated axis of symmetry shown as center line 36. Stud 32 and eyelet 34 may be made of an non-conductive material, such as polymeric plastic, e.g. acrylonitrile-butadine-styrene (ABS), or the like and subsequently coated with a thin continuous coating of electrically conductive material such as silver. Alternatively, the stud and eyelet can be made wholly of a material such as stainless steel or other chemically inert material.

The stud and eyelet are generally well known in the art and include collars 38 and 40, respectively and are adapted to snap together and secure between the collars the label sheet 42 and the electrically-conductive substrate sheet 44. Label sheet 42 is preferably a circular sheet made of a plastic vinyl material centrally disposed about center line 36 and includes an adhesive layer 46 on one side. Substrate sheet 44 is also preferably a circular sheet and centered about center line 36. However, sheet 44 is smaller in diameter than label sheet 42 so that it is secured on one of its sides 48 to adhesive layer 46 with a portion of the adhesive layer 46 being left exposed around the periphery of the sheet 44. Substrate sheet 44 is preferably made of a flexible, electrically-conductive synthetic polymeric sheet material, such as a thermoplastic carbonate-linked polymer manufactured under the trademark Lexan by General Electric Co. of Schenectady, N.Y. and loaded with particles of an electrically-conductive material such as carbon black or silver. The sheet 44 is secured tightly against the collar 40 of eyelet 34 so that relatively good electrical contact is maintained therebetween. The opposite side 50 of sheet 44 is preferably provided with a thin layer 52 of a predetermined amount of an electrically-conductive material, preferably silver, deposited at select locations radially spaced from the center line 36 and in particular the collar 40 of eyelet 34. The particular configuration of the layer 52 on the side 50 of sheet 44 may vary, with a continuous ring centered about center line 36 being preferred. Alternatively, the layer 52 could be disposed in sections spaced from eyelet 34 circumferentially spaced around the center line 36. As shown in FIG. 4, sheet 44 may be provided with one or more notches 54 around the peripheral edge so that an additional portion of adhesive layer 46 is exposed for reasons which will be apparent hereinafter. The amount of material used to form layer 52 is a function of (1) the thickness of the metal, (2) the surface area of the metal interfacing with the electrically conductive, ionically reactive coupling material used with the electrode, (3) the operating DC voltage to be applied to the electrode, (4) the operating DC current level to be used with the electrode, and (5) the optimum time for total consumption of the metal reacting with the electrically-conductive, ionically reactive coupling material as the DC current is transmitted through the electrode. By way of example, where the electrode is to be used with a 2.7 volt lithium battery, at 80 microamps, 0.00037 ounces or approximately 0.0116 grams of silver can be used at a thickness from 250 to 700 microinches to provide approximately 36 hours of optimum time to total consumption. An incidental advantage of providing a predetermined amount of material to form layer 52, is that at the end of the corresponding predetermined amount of time associated with that amount of material, the patient is required to change the electrode so that he can make sure no skin ill effects have occurred, and so that the skin can periodically breath and be cleaned. Thus, when the electrode is used with relatively large DC currents the expiration of the predetermined time period of the useful life of the electrode necessitates removal of the electrode which is consistent with the health and therapeutic techniques of osteogenesis.

Where the eyelet 34 is made of stainless steel an additional eyelet cover sheet 56 having an adhesive coating 58 is secured with the coating over the collar 40 of eyelet 34. The cover sheet 56 is preferably made of a material impervious to the coupling material to be used in the electrode and is sized to completely cover the collar 40 of eyelet 34 so as to protect the eyelet from the coupling material, while leaving exposed the layer 52.

The electrode assembly also preferably includes a thin porous compressible disc or pad 60 centrally disposed about center line 36 and preferably made of an absorbent material such as an open-cell foamed polyurethane or the like. The pad has a diameter which is smaller than the sheet 42 and slightly larger than sheet 44 so that it will completely cover sheet 56 and silver 52 and held in place by exposed portions of the adhesive layer 46 of sheet 42 while leaving a portion of the adhesive layer 46 exposed around the periphery of the pad 60. The pad 60 is preferably preloaded with an electrically-conductive material, such as paste or gel ionically reactive with the layer 52, which electrically couples the electrode to the skin of the user. A suitable coupling material is a gel comprising a sodium chloride salt dissolved in a solution of, for example, agar with other contituents providing the desired predetermined values of conductivity, pH, vicosity and the like. Other chloride solutions can be used such as one containing potassium chloride, or alternatively chloride-free solutions, such as potassium citrate or potassium carboxypolymethylene. The coupling material directly contacts and thus interfaces with layer 52 as prescribed in accordance with one aspect of the present invention.

A ring 62 is centrally disposed about the center line 36. The ring has an outer diameter substantially equal to the outer diameter of sheet 42 and preferably is of a closed cell foamed material having an internal aperture 64 sized to receive the pad 60. Both sides of ring 62 are provided respectively with adhesive layers 66 and 68. Adhesive layer 66 together with the exposed adhesive of layer 46 secure the ring to label sheet 46. The exposed adhesive layer 68 is preferably pressure sensitive adhesive of a hypoallergenic type so that the electrode assembly can be secured with layer 68 to the skin of a living body with reduced skin irritation. The thickness of ring 62 is such that pad 60 will be exposed through aperture 64 and will contact the skin when the electrode assembly 30 is secured to the skin by adhesive layer 68 as shown in FIG. 5. The electrical pathway is thus from the stud member through conductive sheet 44, layer 52, the gel of pad 60 to the skin.

A carrier sheet 70 (shown in FIG. 3), impervious to the gel in pad 60, can be provided over adhesive layer 68 so as to protect the pad and prevent the gel from evaporating. The carrier sheet can be treated with any suitable material, for example, a release agent such as silicone, so that it easily releases from adhesive layer 68.

Figure 6:
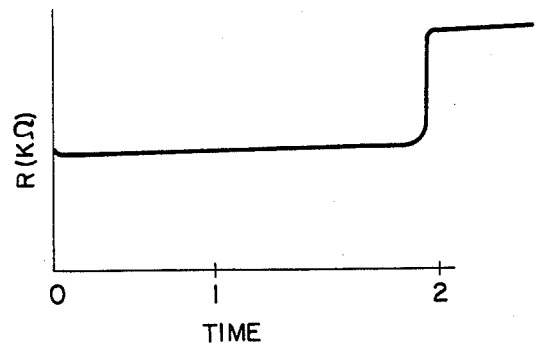
FIG. 6 is a graphical illustration of typical values of resistance of the electrical pathway of the electrode of FIG. 3 as a function of time.

The electrode assembly 30 thus described is made in accordance with the present invention. As constructed, the silver layer 52 will ionically react with the coupling material in pad 60 when subjected to a relatively large DC current, (i.e., in the order of 80 microamps) as previously described. In particular in the case where a chloride gel is used as the coupling material contacting the skin, the silver will ionize and react with the chloride ion to slowly convert the silver of layer 52 into silver chloride. At current levels of 80 microamps the impedance between the sheet 44 and the coupling material will be sufficiently high so that little current flows directly between the sheet and the gel. Accordingly the electron flow primarily occurs from the coupling material provided in pad 60, through layer 52, from layer 52 through sheet 44 to the eyelet 34 of the stud member. The stud member, chemically isolated from the coupling material by cover sheet 56, does not in any way interface with the coupling material so that the stud member will not undergo any ionization reaction. Instead, the reaction occurs at the interface between layer 52 and the coupling material provided in pad 60. Accordingly, the amount of silver can be more efficaciously provided as a function of the intended useful operating life of the electrode as an anode pad. By providing a sufficiently thin silver layer, the resistances offered by the interface between the silver layer and the coupling material will remain substantially constant during the useful operating life of the electrode until the silver is entirely converted to silver chloride as shown at t=2 in FIG. 6.

Figure 7:
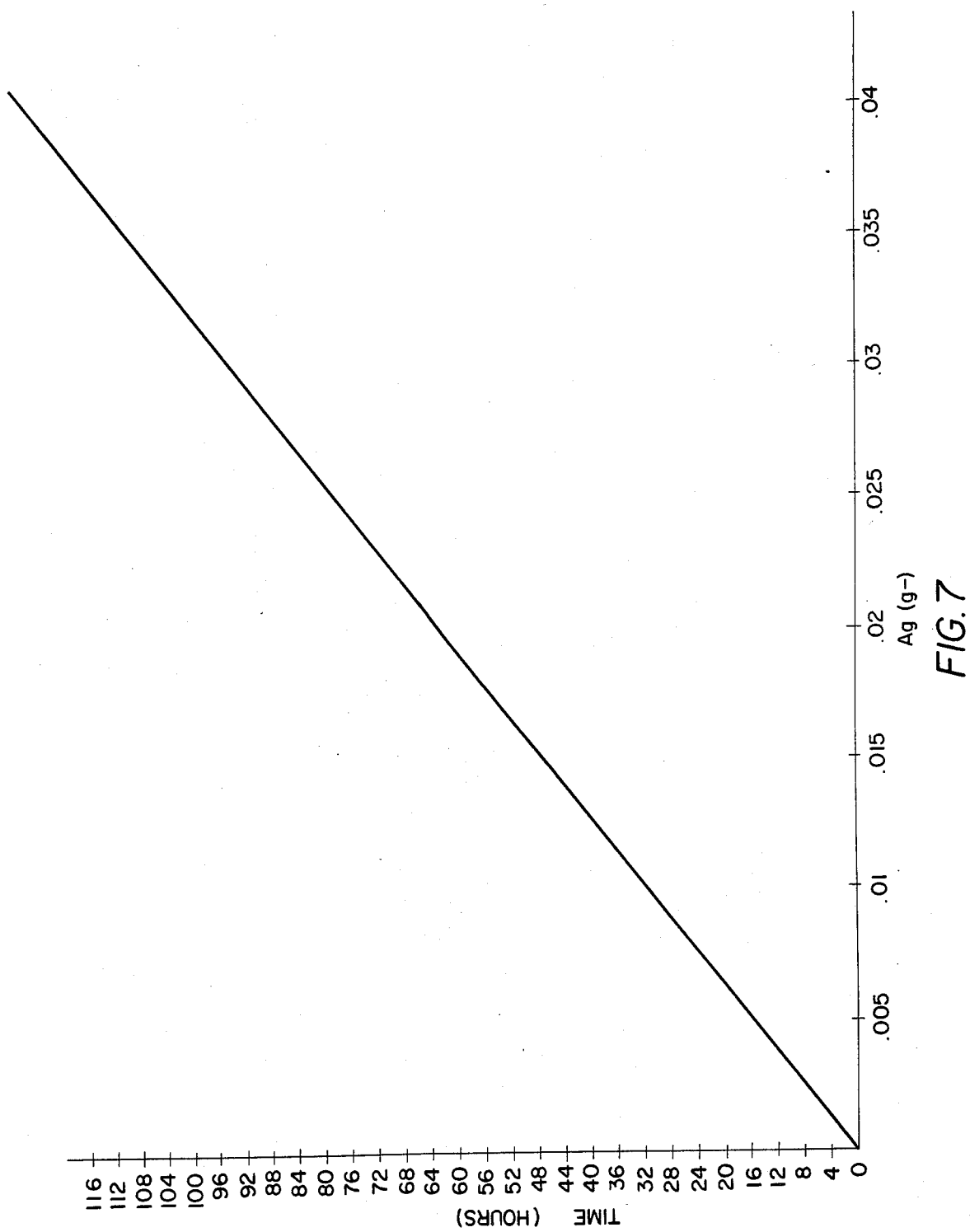
FIG. 7 is a graphical illustration of the amount of silver used in the silver layer of the FIG. 3 embodiment as a function of the useful operating life of the electrode.
Figure 8:
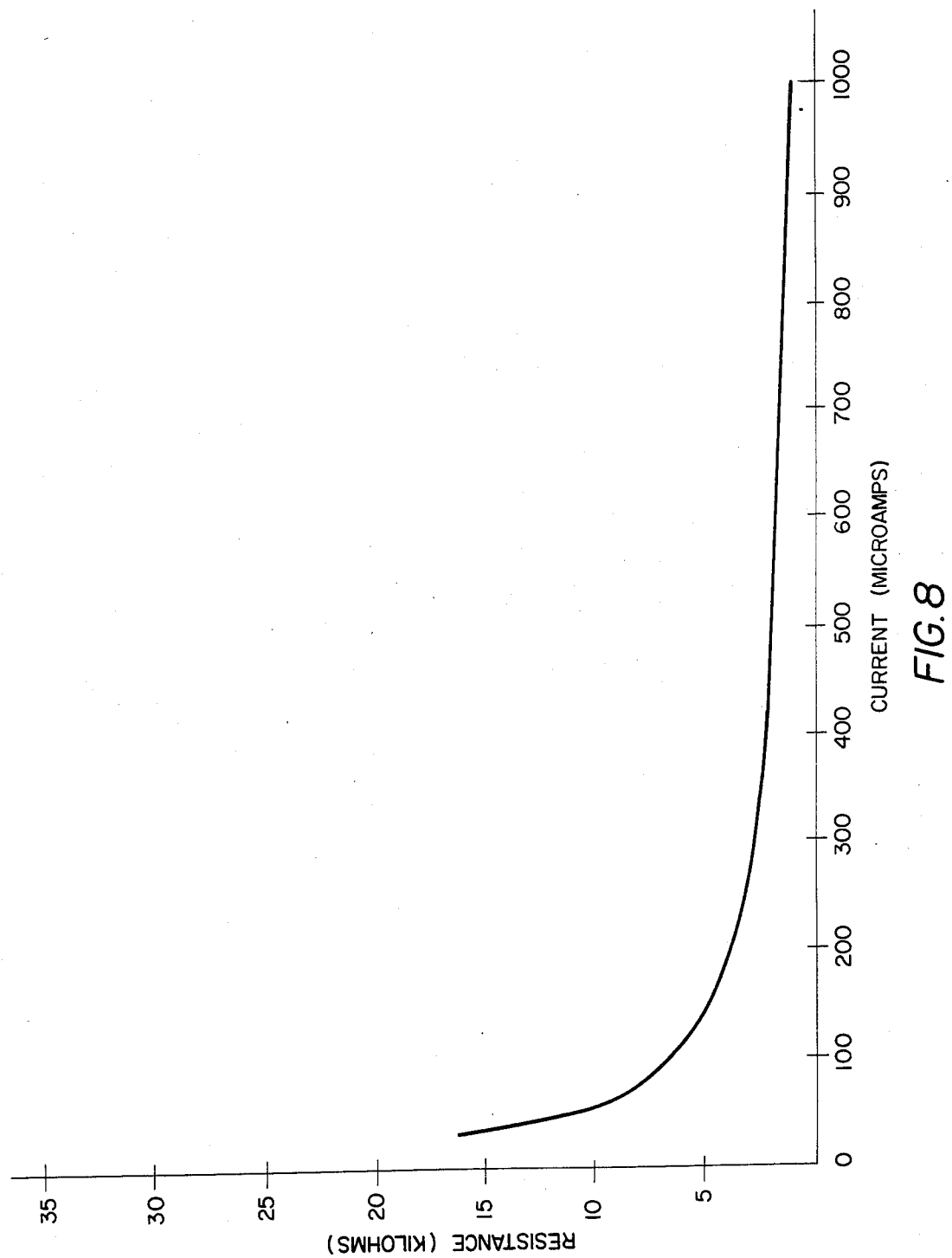
FIG. 8 is a graphical illustration of the operating DC current levels and the resistance of the interface between a chloride ion gel and a predetermined amount of silver.

Referring to FIG. 7 the graph shown was empirically derived and illustrates that, given a precise thickness of silver interfacing a chloride gel, there is an approximate linear relation between the weight of the silver layer 52 and the intended useful operating life of the electrode as an anode pad. The slope of the curve shown is dependent on the level of operating current with a greater slope being provided at smaller current levels. Thus, the electrode structure of the present invention in addition to being useful with relatively high DC current levels (e.g. approximately 80 microamps) can also be used in detecting biological as well as physiological signals at significantly lower levels. The electrode therefore can be used for other purposes such as monitoring and testing applications such as electrocardiographic testing.

Figure 10:
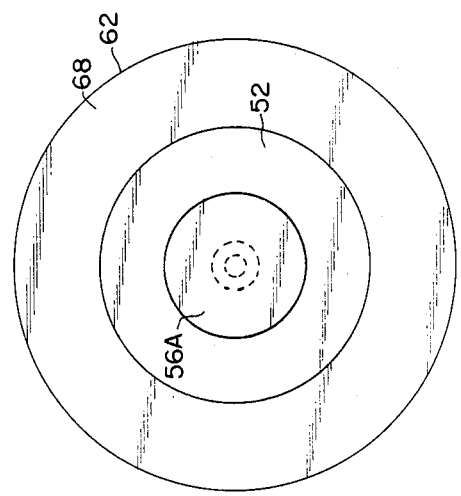
FIG. 10 is a bottom view of the electrode of FIG. 9.
Figure 9:
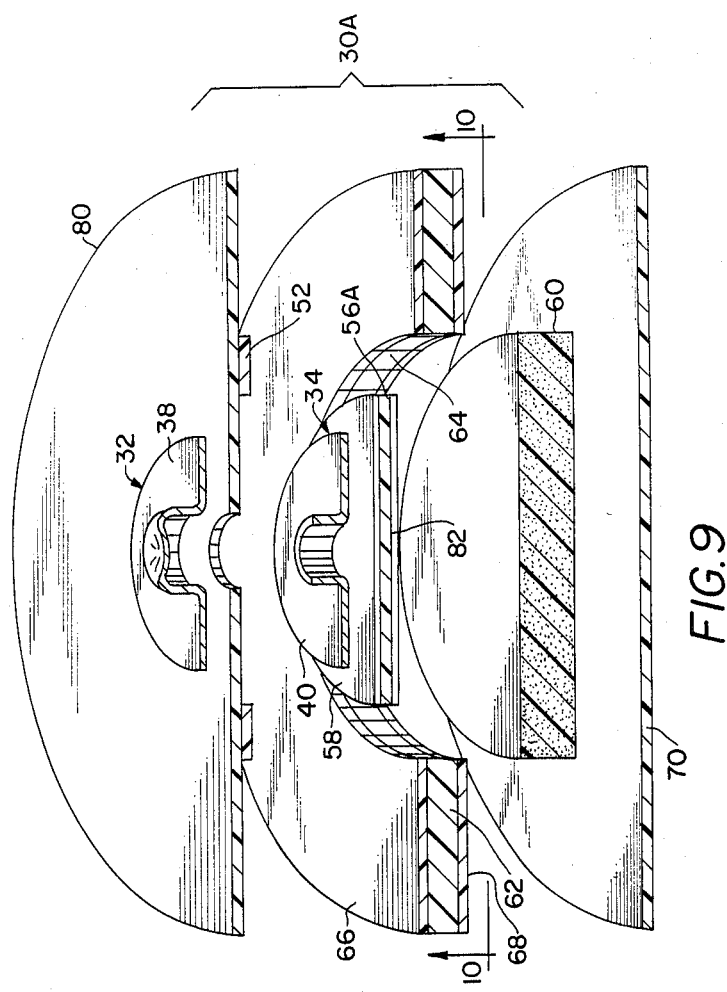
FIG. 9 is an exploded perspective view taken in cross-section of a second embodiment of the electrode of the present invention.

Modifications can be made to the electrode assembly without departing from the scope of the invention. For example, as shown in FIGS. 9 and 10 the label sheet 42 and conductive sheet 44 are combined into a single conductive sheet 80 having disposed thereon the silver 52. The eyelet cover sheet 56 is accordingly provided with a second adhesive coating 82 on the side of sheet 56 opposite that of adhesive coating 58 so that the pad 60 can be centrally positioned thereon. Where the sheet 56 is omitted the pad 60 can be suitably attached directly to sheet 80 with adhesive provided between the silver 52 and collar 40 of eyelet 34.

The electrode assembly of the present invention thus has a more accurately programmable intended useful operating life by controlling the amount of silver of layer 52 deposited on the sheet 50 or 80 than previously provided by the silver coated stud members of the prior art since a greater surface area of the layer interfaces with the ionically-reactive, electrically-conductive coupling material in the pad 60. A further advantage is provided by virtue of the fact that when pressure is applied against the stud member, such as when connecting a lead wire to the stud member, the coupling material is forced radially from the center line 36 toward the conducting interface between layer 52 and the coupling material.

Although the electrode assembly has been described in its preferred form, changes may be made thereto without departing from the invention. For one, the electrode can be of any general shape, e.g. rectangular. Further the protective sheet 56 can be omitted when an eyelet 34, chemically inert to the gel is used.

Since certain other changes may be made in the above product without departing from the scope of the invention herein involved, it is intended that all matter contained in the above description or shown in the accompanying drawings shall be interpreted in an illustrative and not in a limiting sense.

What is claimed is:

1. In a medical electrode of the type including an electrically conductive stud member and a first electrically conductive material for electrically coupling the electrode to skin the improvement comprising:

a substrate including a second electrically conductive material substantially chemically inert with respect to said first electrically conductive material and electrically coupled to said stud member, and a layer of a third electrically conductive material ionically reactive with said first electrically conductive material when current is transmitted therebetween, said layer being disposed on said substrate physically spaced from said stud member and electrically interfacing with said first electrically conductive material so as to define an electrical path from said first electrically conductive material, through said layer to said second electrically conductive material and from said second electrically conductive material to said stud member.

2. A medical electrode according to claim 1, wherein said layer of third electrically conductive material is disposed on said substrate in a pattern radially spaced from said stud member.

3. A medical electrode according to claim 2, wherein said pattern of said layer is a ring disposed concentrically around said stud member.

4. A medical electrode according to claim 3, wherein said substrate and said stud member are secured together.

5. A medical electrode according to claim 1, wherein said layer of said third electrically conductive material is of a predetermined thickness and weight.

6. A medical electrode according to claim 5, wherein said third electrically conductive material is silver.

7. A medical electrode according to claim 6, wherein said first electrically conductive material includes negative ions and said silver ionically reacts with said negative ions as a function of time when a DC current is transmitted along said electrical path, wherein said predetermined thickness and weight is selected in part as a function of the expected level of said DC current so that said layer completely reacts with said first electrically conductive material at predetermined useful operating life.

8. A medical electrode according to claim 7, wherein said negative ions are chloride ions and said layer reacts with said chloride ions to form silver chloride when a DC current is transmitted along said electrical path.

9. A medical electrode according to claim 1, further including a sheet impervious to said first electrically conductive material disposed between said stud member and said first electrically conductive material.

10. A medical electrode according to claim 1, further including a removable carrier sheet impervious to said first electrically conductive material and a porous pad which contains said first electrically conductive material and is in contact with said carrier sheet.

11. A medical electrode according to claim 10, further including a ring of material secured to said substrate and having an aperture which receives said pad.

12. A medical electrode according to claim 1, wherein said substrate includes an electrically conductive synthetic polymeric material.

* * * * *